United States Patent
Frinking et al.

(10) Patent No.: US 6,962,071 B2
(45) Date of Patent: Nov. 8, 2005

(54) METHOD FOR IMPROVED MEASUREMENT OF LOCAL PHYSICAL PARAMETERS IN A FLUID-FILLED CAVITY

(75) Inventors: Peter J. A. Frinking, Geneva (CH); Marcel Arditi, Geneva (CH)

(73) Assignee: Bracco Research S.A., Geneva (CH)

( * ) Notice: Subject to any disclaimer, the term of this patent is extended or adjusted under 35 U.S.C. 154(b) by 5 days.

(21) Appl. No.: 10/474,134

(22) PCT Filed: Apr. 5, 2002

(86) PCT No.: PCT/IB02/01229

§ 371 (c)(1),
(2), (4) Date: Oct. 3, 2003

(87) PCT Pub. No.: WO02/080774

PCT Pub. Date: Oct. 17, 2002

(65) Prior Publication Data

US 2004/0129082 A1 Jul. 8, 2004

Related U.S. Application Data

(60) Provisional application No. 60/281,794, filed on Apr. 6, 2001.

(51) Int. Cl.[7] .............................. G01V 1/40; G01N 7/00; A61B 8/00
(52) U.S. Cl. ..................... 73/24.01; 73/64.53; 73/602; 600/438; 600/458
(58) Field of Search ....................... 73/579, 602, 19.03, 73/19.1, 24.01, 24.06, 29.05, 31.05, 32 A, 54.41, 64.53; 600/437, 438, 458

(56) References Cited

U.S. PATENT DOCUMENTS

| | | |
|---|---|---|
| 4,093,709 A | 6/1978 | Choi et al. |
| 4,131,648 A | 12/1978 | Choi et al. |
| 4,138,344 A | 2/1979 | Choi et al. |
| 4,180,646 A | 12/1979 | Choi et al. |
| 4,483,345 A | 11/1984 | Miwa |
| 4,675,381 A | 6/1987 | Bichon et al. |
| 4,718,433 A | 1/1988 | Feinstein |
| 4,844,882 A | 7/1989 | Widder et al. |
| 4,888,398 A | 12/1989 | Bichon et al. |
| 4,892,733 A | 1/1990 | Bichon et al. |

(Continued)

FOREIGN PATENT DOCUMENTS

| | | |
|---|---|---|
| DE | 2946662 A1 | 5/1981 |
| EP | 0 122 624 B1 | 9/1988 |
| EP | 0 123 235 B1 | 9/1988 |

(Continued)

OTHER PUBLICATIONS

"Noninvasive assessment of pressure gradients across iliac artery stenoses: duplex and catheter correlative study" (J Ultras Med 1993; 12:17–22) by Strauss et al.

(Continued)

*Primary Examiner*—Hezron Williams
*Assistant Examiner*—Rose M. Miller
(74) *Attorney, Agent, or Firm*—M. Caragh Noone

(57) ABSTRACT

The present invention relates to remotely determining local physical parameters in a fluid-filled cavity (e.g. heart cavities, blood vessels, industrial container) by means of ultrasound waves and encapsulated or stabilised gas bubbles. A measuring method, a method of diagnostic ultrasound of the same and an apparatus for remotely determining ambient physical local parameters of a fluid-filled cavity are disclosed.

15 Claims, 7 Drawing Sheets

U.S. PATENT DOCUMENTS

| | | | |
|---|---|---|---|
| 4,900,540 A | | 2/1990 | Ryan et al. |
| 5,137,928 A | | 8/1992 | Erbel et al. |
| 5,230,882 A | | 7/1993 | Unger |
| 5,271,928 A | | 12/1993 | Schneider et al. |
| 5,380,519 A | | 1/1995 | Schneider et al. |
| 5,413,774 A | | 5/1995 | Schneider et al. |
| 5,445,813 A | | 8/1995 | Schneider et al. |
| 5,529,766 A | | 6/1996 | Klaveness et al. |
| 5,531,980 A | | 7/1996 | Schneider et al. |
| 5,536,490 A | | 7/1996 | Klaveness et al. |
| 5,556,610 A | | 9/1996 | Yan et al. |
| 5,558,857 A | | 9/1996 | Klaveness et al. |
| 5,567,414 A | | 10/1996 | Schneider et al. |
| 5,578,292 A | | 11/1996 | Schneider et al. |
| 5,580,575 A | | 12/1996 | Unger et al. |
| 5,597,549 A | | 1/1997 | Schneider et al. |
| 5,607,661 A | | 3/1997 | Berg et al. |
| 5,637,289 A | | 6/1997 | Klaveness et al. |
| 5,643,553 A | | 7/1997 | Schneider et al. |
| 5,658,551 A | | 8/1997 | Schneider et al. |
| 5,686,060 A | | 11/1997 | Schneider et al. |
| 5,711,933 A | | 1/1998 | Bichon et al. |
| 5,749,364 A | * | 5/1998 | Sliwa et al. ............... 600/438 |
| 5,798,091 A | | 8/1998 | Trevino et al. |
| 5,827,504 A | | 10/1998 | Yan et al. |
| 5,846,518 A | | 12/1998 | Yan et al. |
| 5,911,972 A | | 6/1999 | Schneider et al. |
| 5,919,434 A | | 7/1999 | Dugstad et al. |
| 5,990,263 A | | 11/1999 | Dugstad et al. |
| 6,224,554 B1 | * | 5/2001 | Tickner et al. ............. 600/438 |
| 6,302,845 B2 | * | 10/2001 | Shi et al. .................... 600/438 |
| 6,322,512 B1 | * | 11/2001 | De Jong et al. ............ 600/458 |
| 2002/0194907 A1 | * | 12/2002 | Bostrom et al. ......... 73/152.58 |

FOREIGN PATENT DOCUMENTS

| | | |
|---|---|---|
| EP | 0 365 467 B1 | 8/1993 |
| EP | 0 324 938 B1 | 11/1993 |
| EP | 0 296 189 B1 | 1/1994 |
| EP | 0 474 833 B1 | 8/1995 |
| EP | 0 554 213 B1 | 1/1997 |
| EP | 0 619 743 B1 | 1/1997 |
| EP | 0 744 962 B1 | 9/2001 |
| EP | 0 682 530 B1 | 3/2003 |
| EP | 0 881 915 B1 | 4/2003 |
| WO | WO 93/13809 A1 | 7/1993 |
| WO | WO 95/01187 A1 | 1/1995 |
| WO | WO 95/21631 A1 | 8/1995 |
| WO | WO 96/15815 A1 | 5/1996 |
| WO | WO 97/29783 A1 | 8/1997 |
| WO | WO 98/32378 A1 | 7/1998 |
| WO | WO 99/47045 A1 | 9/1999 |

OTHER PUBLICATIONS

"A new noninvasive technique for cardiac pressure measurement: resonant scattering of ultrasound from bubbles" (IEEE Trans Biomed Eng 1977; 24:107–110;) Fairbank et al.

"A new approach to noninvasive manometry: interaction between ultrasound and bubbles" (Med Biol Eng Comput 1981; 19:35–39; by Hölt.

"New approach to noninvasive manometry based on pressure dependent resonant shift of elastic microcapsules in ultrasonic . . . characteristics" (Jap J App Phys 1988; 27:125–127) by Ishihara et al.

"Noninvasive measurement of the hydrostatic pressure in a fluid–filled cavity based on the . . . Bubbles" (Bouakaz et al.–Ultrasound in Medicine and Biology 1999; 25:1407–1415).

"Pressure dependence of subharmonic signals from contrast microbubbles" (Ultrasound in Medicine and Biology 1999; 25:275–283–Shi et al.).

"Scattering properties of encapsulateed gas bubbles at high ultrasound pressures"0 (Journ. Accoust. Soc. Am. 1999:105; 1989–1996–Frinking et al.).

"The Mannich bases in polymer synthesis: 3. Reduction of Poly (beta–aminoketone)s to poly (Gamma –aminoalcohol)s . . . "(Polymer 23 (1982), 1693) by Angeloni et al.

"Chemical and Physical Structure of Polymers as Carriers for Controlled Release of Bioactive Agents" (R. Langer et al, Macromol. Chem. Phys. C23 (1983), 61–126).

PCT Search Report for PCT/IB02/01229 mailed Nov. 15, 2002.

"Cardiac Pressure and Flow Measurements" (E. Glenn Tickner), in "Precision microbubbles for right side intracardiac pressure and flow measurements" (Meltzer RS and Roelandt JTCR, ed. Contrast echocardiography; London: Martinus Nijhoff, 1982; 15:313–324; Ishihara K et al.).

"Controlled release of biologiclly active compounds from bioerodible polymers" (J. Heller–Biomaterials 1 (1980), 51–57).

"Polyphosphazenes: New Polymers with Inorganic Backbone Atoms" (Harry R. Allcock–Science 193 (1976), 1214–1219).

* cited by examiner

METHOD FOR IMPROVED MEASUREMENT OF LOCAL PHYSICAL PARAMETERS IN A FLUID-FILLED CAVITY

This application claims the benefit of provisional application 60/281,794 filed on Apr. 6, 2001.

TECHNICAL FIELD

The present invention relates to a noninvasive measuring method for remotely determining local physical parameters of a fluid-filled cavity, by means of ultrasound waves and encapsulated or stabilized gas bubbles (e.g. suspensions of stabilized microbubbles, microballoons or microparticles comprising gas).

BACKGROUND OF THE INVENTION

Physiological parameters of the cardiovascular system, such as blood pressure, temperature and gas concentration are important since they provide essential information concerning the state of health of organs and the patient. Currently, dynamic blood pressure measurements are mainly performed by catheterization, consisting of a pressure-sensing catheter that is inserted into the heart chamber or blood vessel, or by Doppler echocardiography using the simplified Bernoulli equation (Burton C. Physiology and biophysics of the circulation. $2^{nd}$ edition. Chicago, 1972). The first method is accompanied by the disadvantages of an invasive procedure, i.e. creating pain and risk of infection. The second, noninvasive method does not provide reliable or reproducible blood pressure values (Strauss A L, Roth F J, Rieger H. "Noninvasive assessment of pressure gradients across iliac artery stenoses: duplex and catheter correlative study" *J Ultras Med* 1993; 12: 17–22).

Alternative techniques are described in the literature and are mainly based on the interaction of ultrasound waves with individual gas bubbles (Fairbank W, Scully M. "A new noninvasive technique for cardiac pressure measurement: resonant scattering of ultrasound from bubbles" IEEE Trans Biomed Eng 1977; 24: 107–110; Hök B. "A new approach to noninvasive manometry: interaction between ultrasound and bubbles" *Med Biol Eng Comput* 1981; 19: 35–39; Tickner E G. "Precision microbubbles for right side intracardiac pressure and flow measurements" *Meltzer RS and Roelandt JTCR*, ed. Contrast echocardiography; London: Martinus Nijhoff, 1982; 15: 313–324; Ishihara K et al. "New approach to noninvasive manometry based on pressure dependent resonant shift of elastic microcapsules in ultrasonic frequency characteristics" *Jap J App Phys* 1988; 27: 125–127; DE 29 46 662 A1 (Siemens AG); EP 0 296 189 B (Schering AG); U.S. Pat. No. 4,483,345 (Miwa).

Due to the high compressibility of gas, the size of a gas bubble changes as a function of the local hydrostatic pressure. This change in size affects the acoustic characteristics of the gas bubble, like resonance frequency, scattering and attenuation cross-section, etc. Therefore, the local pressure in a fluid-filled cavity can be derived from these acoustic characteristics.

Recent attempts to utilize gas bubbles to noninvasivaly assess the pressure in fluid filled cavities (De Jong et al. WO 98/32378 (Andaris Ltd.); Shi et al. WO 99/47045) have been hampered by inaccuracy and insensitivity De Jong et al. WO 98/32378 (Andaris Ltd.) and Bouakaz et al. ("Noninvasive measurement of the hydrostatic pressure in a fluid-filled cavity based on the disappearance time of micrometer-sized free gas bubbles" *Ultrasound in Medicine and Biology* 1999; 25: 1407–1415) disclosed a method for noninvasive measurement of the local pressure involving injection of what are referred to as gas containing microcapsules into the circulatory system. By transmitting a low frequency, high amplitude ultrasound burst, free-gas bubbles are released from the gas containing microcapsules into the region where the local pressure is to be measured. The disappearance time of the released free gas depends on the local pressure and is used for noninvasive determination of the local pressure. In this application, the total response of the released gas bubbles (fundamental and second harmonic) is used to calculate the disappearance time. The Bouakaz article stated that this method is inaccurate for detecting small pressure changes on the order of 5–10 mmHg, which are clinically relevant (Bouakaz et al. "Noninvasive measurement of the hydrostatic pressure in a fluid-filled cavity based on the disappearance time of micrometer-sized free gas bubbles" *Ultrasound in Medicine and Biology* 1999; 25: 1407–1415).

Shi et al. WO 99/47045, stated that an excellent correlation exists between the amplitude of subharmonic signals generated by microbubbles and the local pressure. Thus, they suggested that sub and ultraharmonic amplitude may be used to noninvasivaly to estimate the local pressure, asserting that subharmonic amplitudes are a much better indicator of pressure variation than fundamental and second harmonic amplitudes. However, the difference in sub- and/or ultraharmonic amplitude is very small for pressure changes ranging from 5–10 mmHg (Shi et al. "Pressure dependence of subharmonic signals from contrast microbubbles" *Ultrasound in Medicine and Biology* 1999; 25: 275–283). Therefore, this method is also lacking sensitivity when detecting small pressure changes. Secondly, this method strongly depends on the size of the bubbles at the location where the pressure is to be measured. In the method disclosed in WO99/47045, after injection of the bubbles the size distribution will change due to lung filtration and microbubble uptake. Therefore, the exact size of the bubbles, and consequently the acoustic characteristics like sub- and ultraharmonic-response, at the location of interest is unknown.

It is an object of the present invention to provide a new method for accurate and sensitive, noninvasive measurement of the local physical parameters in a fluid-filled cavity. With this new method small pressure changes (5–10 mmHg) can be measured, which is the main limitation of the methods described by aforementioned references. Additionally, unlike the method disclosed in WO99/47045, in the present method, the size of the bubbles at the location where the pressure is to be measured can be better controlled and, therefore, the acoustic characteristics of the bubbles at the site of interest are better specified, which makes the present invention more accurate. With reference to WO98/32378, the present invention entails shorter acquisition time, which makes it more efficient and more useful in the clinic.

This new method can provide clinicians with a valuable tool for determining the state of health of an organ without the risk of infection and with minimal patient discomfort. Moreover, it will be readily apparent to those skilled in the art that the present invention can be used as a general technique for remotely sensing physical parameters, for example in situations where direct measurement is impossible or too dangerous.

SUMMARY OF THE INVENTION

It is an object of the present invention to provide a technique for determining local physical parameters in a fluid-filled cavity by administering stabilized or encapsulated gas bubbles and monitoring the sub- and/or ultraharmonic response of the free gas bubbles released from these stabilized or encapsulated gas bubbles as a function of time.

The stabilized or encapsulated gas bubbles useful in the invention may be divided into several categories:stabilized gasmicrobubbles, gas-filled microcapsules/microballoons, and gas containing microparticles according to the definitions given in for example, in EP 554213 and U.S. Pat. No. 5,413,774.

The term "microbubble" specifically designates gas bubbles, in suspension in a liquid preferably also containing surfactants or tensides to control the surface properties and the stability of the bubbles. The term "microcapsule" or "microballoon" designates preferably air or gas-filled bodies with a material boundary or envelope, i.e. a polymer membrane wall. The term microparticle refers to gas-containing solid systems, for example microparticles (especially aggregates of microparticles) having gas contained therein or otherwise associated therewith (for example being adsorbed on the surface thereof and/or contained within voids, cavities or pores therein).

Free-gas bubbles, i.e. gas bubbles that are not stabilized by any means (gas bubbles which are neither stabilized by tensides or surfactants nor encapsulated by, for example, a polymer or contained in or associated with solids) are obtained from these stabilized or encapsulated gas bubbles by the destruction of the stabilized microbubbles, microballoons or microparticles by, for example, application of one or more ultrasound pulsed waves. The released free gas bubbles dissolve in the surrounding liquid. Consequently, the bubbles shrink and the sub- and/or ultraharmonic response, which is very sensitive to bubble size, changes as a function of time. The time for a gas bubble to completely dissolve in the surrounding liquid is a function of local parameters like gas concentration, temperature and pressure. Therefore, by monitoring the changes in sub- and/or ultraharmonic response of a free gas bubble as a function of time, these parameters can be measured non-invasively.

The sub- and ultraharmonic responses of gas bubbles are very sensitive to their sizes. Consequently, the sub- and ultraharmonic responses of free gas bubbles are very sensitive to parameters that influence the bubble size. Therefore, by measuring the change in bubble size due to gas dissolving in the surrounding liquid, by means of the response of sub- and/or ultraharmonics as a function of time, an estimation of the local pressure or other parameters can be made.

DETAILED DESCRIPTION

Figure 1:
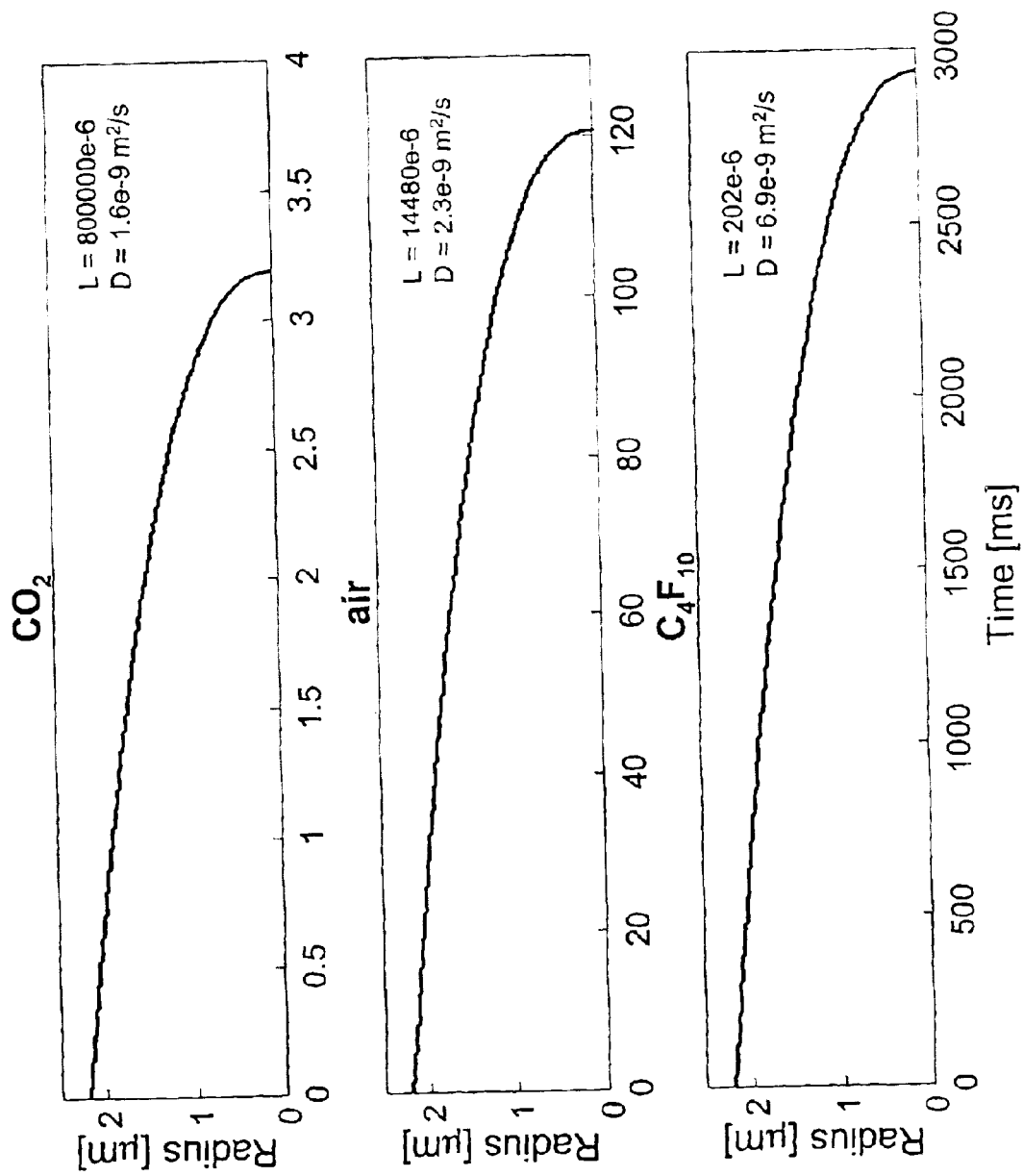
FIG. 1. Radius-time curves for a 2.2-$\mu$m bubble of different gases in water calculated by using equation (1).

One aspect of the present invention is to provide a noninvasive measuring method for remotely determining local physical parameters of a fluid-filled cavity, based on the combined use of encapsulated or stabilized gas bubbles and ultrasound waves, said measuring method comprising the steps of:

a) administering stabilized or encapsulated gas bubbles to a fluid filled cavity;

b) applying with a transducer a first ultrasound pulsed wave or a train of pulsed waves to the fluid filled cavity to destroy the stabilized or encapsulated gas bubbles and generate free gas bubbles c) applying with a transducer a second ultrasound pulsed wave or train of pulsed waves at a frequency specifically chosen for exciting the sub- and/or ultraharmonic response of the bubbles d) determining the mean response time.

e) determining a value for a local physical parameter on the basis of the response time of step d)

It should be mentioned that the improved sensitivity for noninvasive measurement in a fluid-filled cavity as shown in this invention would not be obtainable by omitting one of the steps previously described.

For a better understanding of the invention, the local physical parameters considered here are the pressure, the temperature or the gas concentration.

Surprisingly, it has been found that the essential features of the invention lie in that the sub- and/or ultraharmonic responses of step b) are monitored as a function of time by successive ultrasound pulses, this function being an indication of the local physical parameter being measured. The method of the present invention provides improved accuracy and efficiency by measuring the sub- and ultraharmonic response as a function of time.

The first ultrasound pulsed wave or train of pulsed waves is tuned in such a way (e.g. by adjusting its frequency and/or amplitude) that the size of the released free-gas bubbles is larger than the subharmonic size (as defined later in the specification).

Preferably, the frequency and amplitude of the first ultrasound pulsed wave or train of pulsed waves, to optimize gas release, can be chosen independently of the second ultrasound pulsed wave or train of pulsed waves, used for monitoring the sub- and/or ultraharmonic response.

Preferably, the frequency and amplitude of the second ultrasound pulsed wave or train of pulsed waves, used for monitoring the sub- and/or ultraharmonic response, can be chosen independently of the first ultrasound pulsed wave or train of pulsed waves, to optimize gas realise.

The transducer used to apply the first ultrasound pulsed wave or train of pulsed waves can be the same as or distinct from that used for applying the second ultrasound pulsed wave or train of pulsed waves.

Viewed from a further aspect, the invention provides a method of diagnostic ultrasound for determining local physical parameters of a fluid-filled cavity in situ, which comprises the steps of:

a) administering to a subject a fluid agent comprising encapsulated or stabilised gas bubbles b) applying with a transducer a first ultrasound pulsed wave or a train of pulsed waves to generate free-gas bubbles c) applying with a transducer a second ultrasound pulsed wave or train of pulsed waves around a frequency specifically chosen for exciting the sub- and/or ultraharmonic response of the bubbles d) determining the mean response time e) determining a value for a local physical parameter on the basis of the response time of step d)

characterised in that the sub- and/or ultraharmonic responses of step c) are monitored as a function of time by successive ultrasound wave pulses, this function being an indication of the physical parameter being measured.

According to this method, said subject is a vertebrate, and said fluid agent containing encapsulated or stabilised gas bubbles is introduced into the vasculature or into a body cavity of said vertebrate.

Viewed from a further aspect, the invention provides an apparatus for carrying out the above method of measurement. This apparatus comprises elements found in ultrasound equipment, coupled with a specific software to generate the required excitations and monitoring transmit-pulse sequences, plus the signal-processing functions required for interpreting the observed responses as a function of the local physical parameters. The apparatus includes for example: timing circuits, at least one pulse or arbitrary waveform generator with amplifier, at least one transmit-transducer capable of projecting an ultrasound wave into the region of interest, at least one receive-transducer sensitive to the reflected ultrasound waves, at least one receiving circuit dedicated to the amplification and conditioning of the echo signals, analog or digital circuits dedicated to perform filtering of the echo responses from microbubbles, a Central Processing Unit capable of performing the required computations and comparisons with look-up tables to derive values of the local physical parameters, a memory for storing the required programs, look-up tables, signal data and computed values, and display means for presenting the computed values in a graphical or textual form.

In summary, the objective of the present invention relates to the remote measurement of local physical parameters in a fluid-filled cavity (e.g. heart cavities, blood vessels, industrial container, etc.) by means of ultrasound waves and encapsulated or stabilized gas bubbles, which are used as a vehicle for delivering free-gas bubbles to a site of interest. Stabilisation or encapsulation of the gas, by means of, for example, stabilizing with a tenside or surfactant, encapsulating a gas bubble by a wall or shell, or associating it with a solid prevents the gas content from rapidly dissolving in the surrounding liquid. At the site of interest, where for example the local pressure or other local parameters (like temperature, gas concentration, etc.) are to be measured, the stabilized or encapsulated structure is ruptured by means of ultrasound waves and the gas content is subsequently released. The release can be optimally tuned for releasing known-size free-gas bubbles e.g. by adjusting the frequency and/or the amplitude of the applied ultrasound wave (Frinking et al. "Scattering properties of encapsulated gas bubbles at high ultrasound pressures" *Journ. Acoust. Soc. Am.* 1999: 105; 1989–1996). Surprisingly, it has been found that free-gas bubbles are more susceptible to changes in environmental conditions, like changes in temperature, gas concentration or local pressure, compared to stabilized or encapsulated gas bubbles.

It is known that the radius of a free-gas bubble changes as a function of time according to:

$$\frac{dR}{dt} = \frac{DL}{R} \left( \frac{\frac{C_i}{C_0} - 1 - \frac{2\sigma}{RP_0} - \frac{p_{ov}}{P_0}}{1 + \frac{4\sigma}{3RP_0}} \right) \quad (1)$$

where
R=radius of the bubbles
t=time
D=diffusion constant $C_i/C_o$=ratio of the dissolved gas concentration to the saturation concentration
σ=surface tension
$P_0$=atmospheric pressure
L=Ostwald coefficient
$p_{ov}$=overpressure.

The time for a free-gas bubble to completely dissolve in the surrounding liquid, i.e. the disappearance time, depends on the type of gas. This is reflected in equation (1) by the Ostwald coefficient and diffusion constant of a gas. For example, for a 2.2-μm gas bubble the disappearance time is 3.2 ms for $CO_2$, 120.8 ms for air and 2936.6 ms for $C_4F_{10}$ (FIG. 1).

Figure 2:
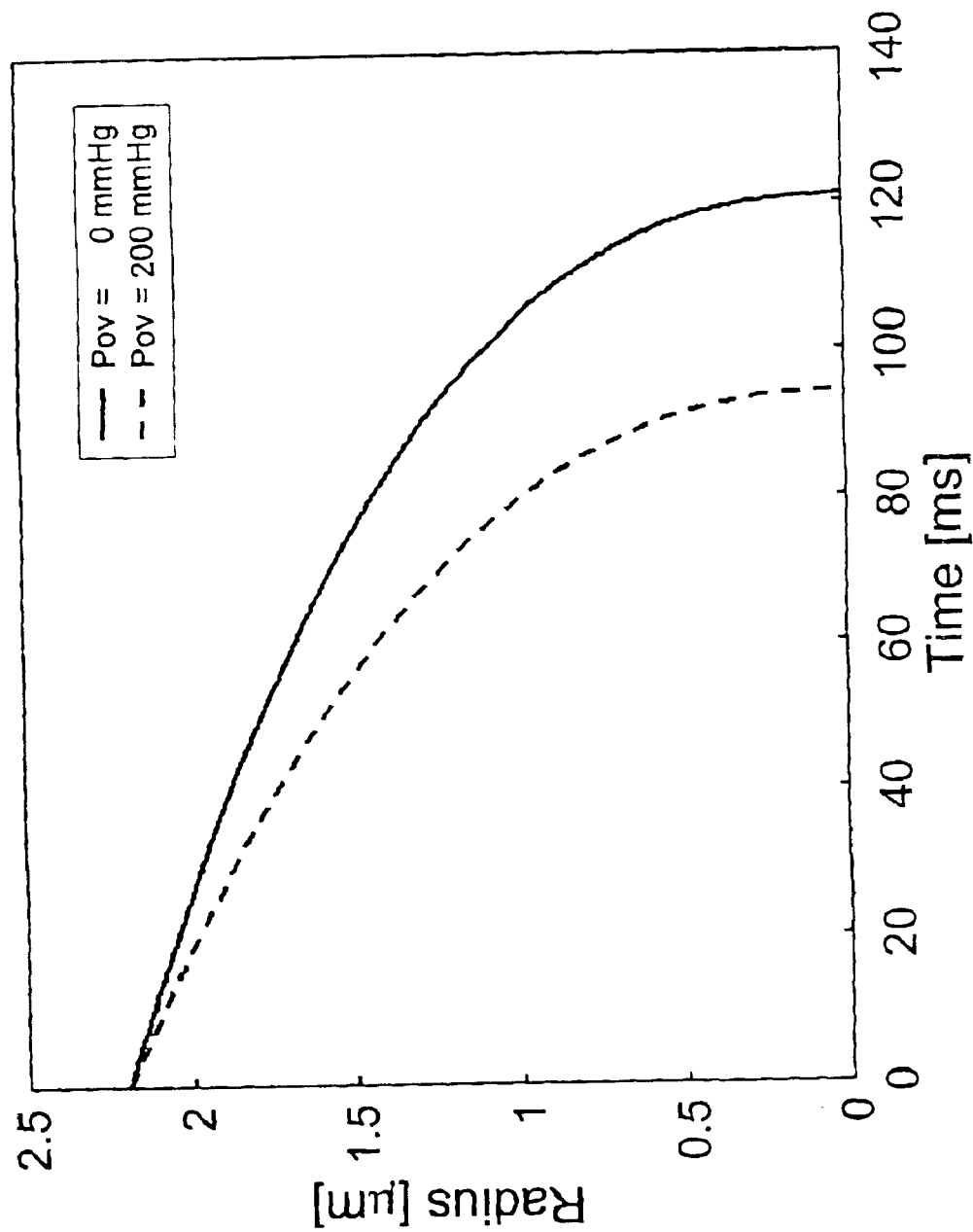
FIG. 2. Radius-time curves for a 2.2-$\mu$m air bubble in water at 0 and 200 mmHg overpressure, calculated by using equation (1).
Figure 3A:
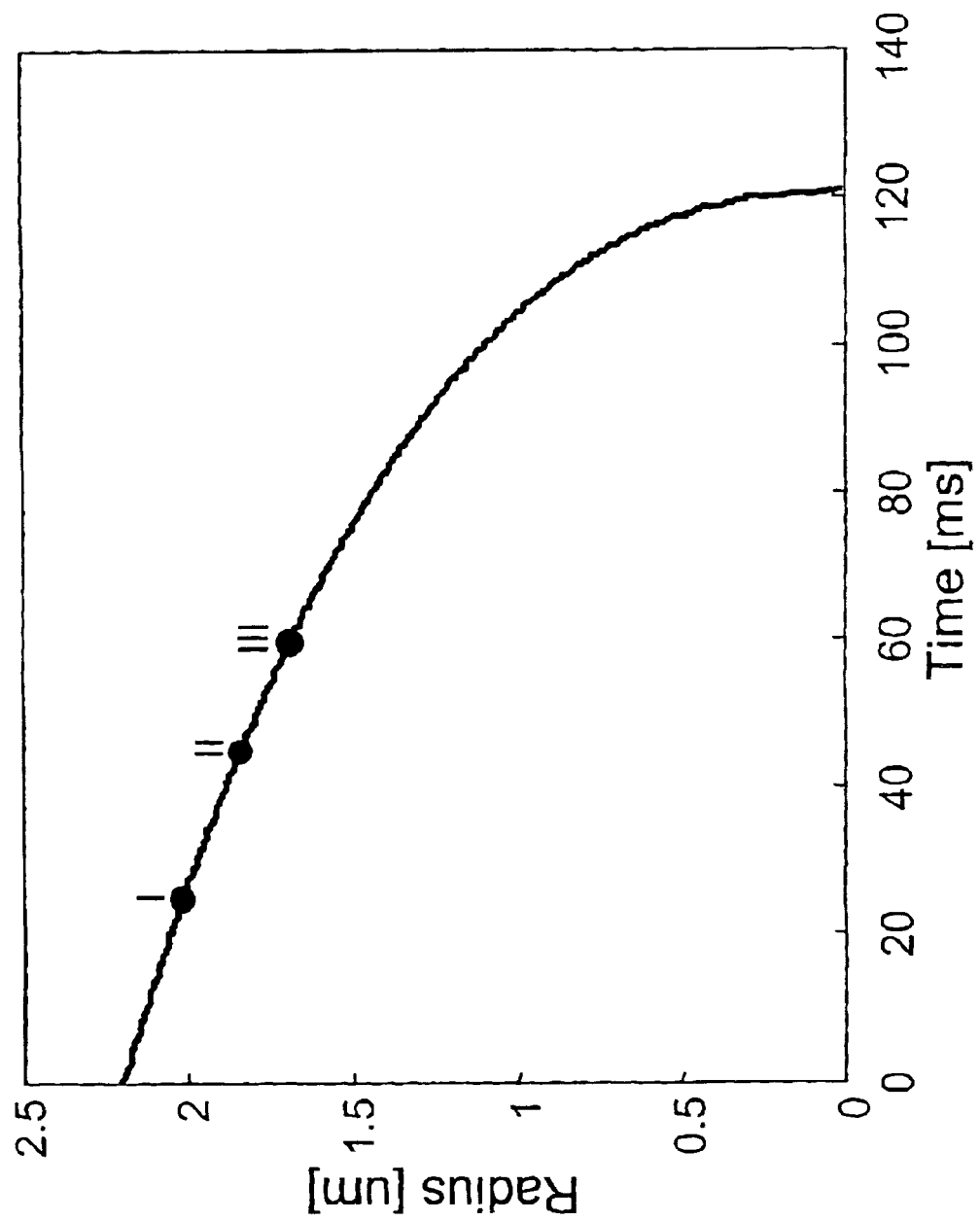
FIG. 3A. Radius-time curves for a 2.2-$\mu$m air bubble in water at 0 mmHg overpressure, calculated by using equation (1).
Figure 3B:
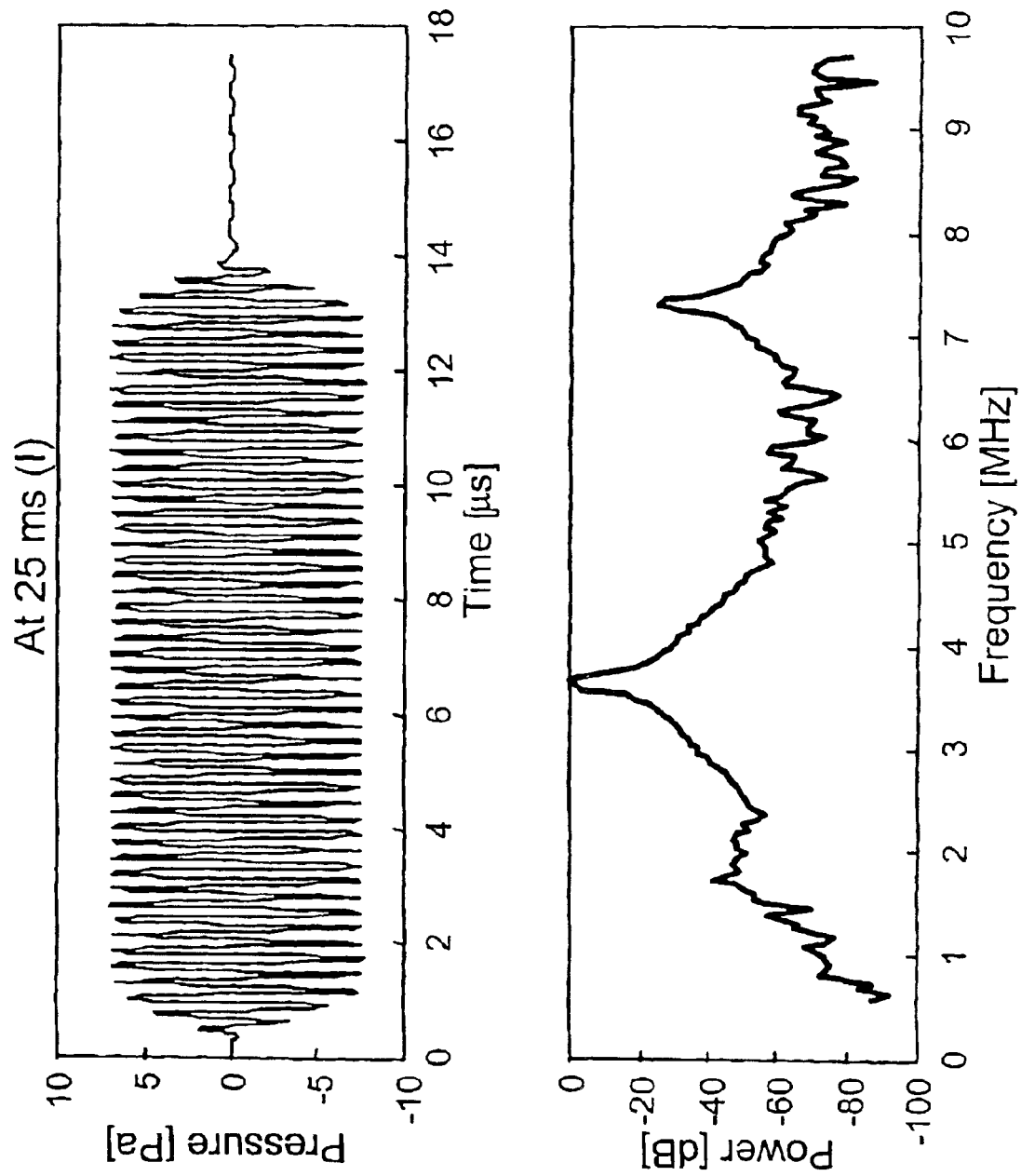
FIG. 3B. Sub- and ultraharmonic response and associated spectrum of a 2.2-$\mu$m air bubble, 25 ms after release.
Figure 3C:
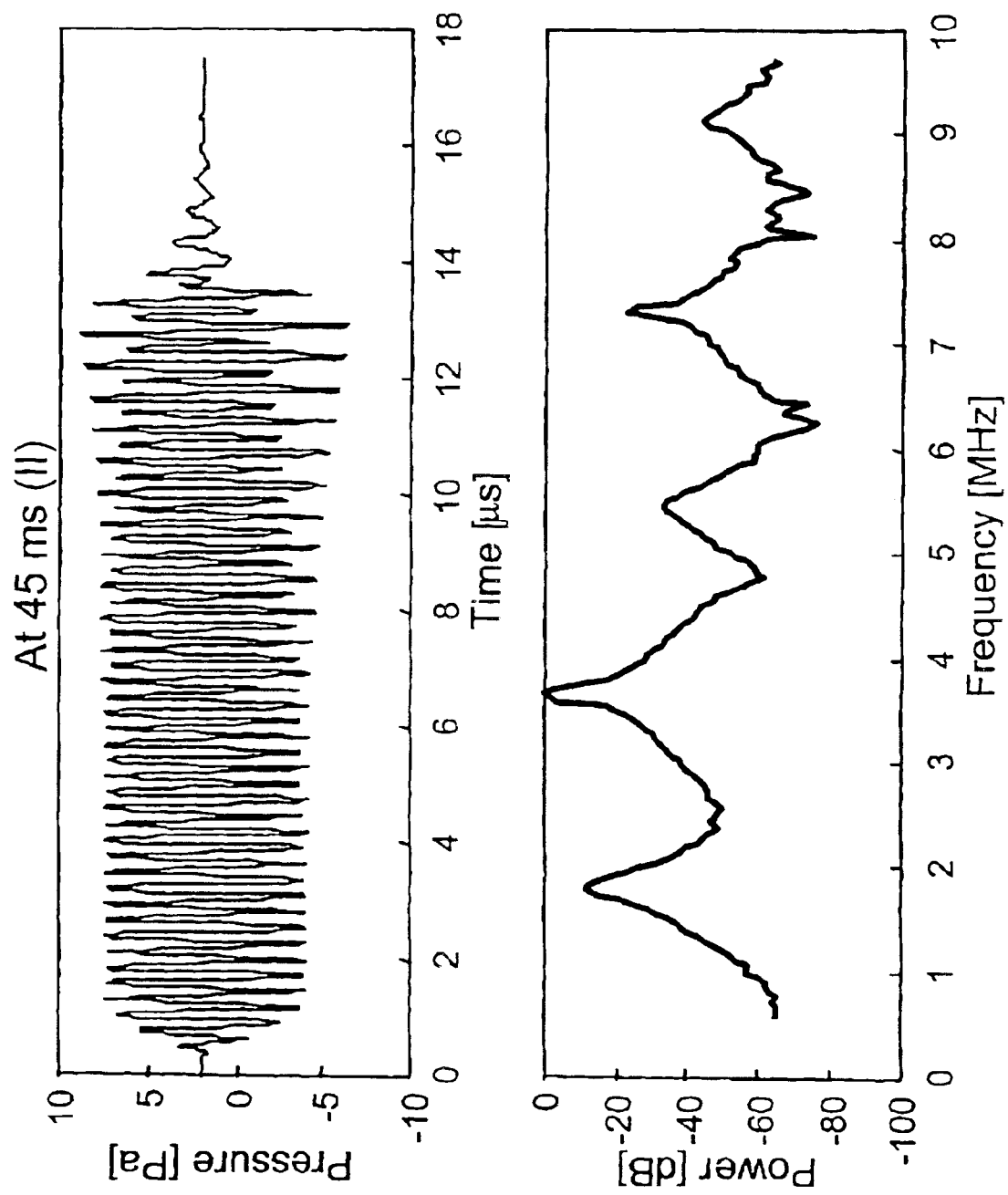
FIG. 3C. Sub- and ultraharmonic response and associated spectrum of a 2.2-$\mu$m air bubble, 45 ms after release.
Figure 3D:
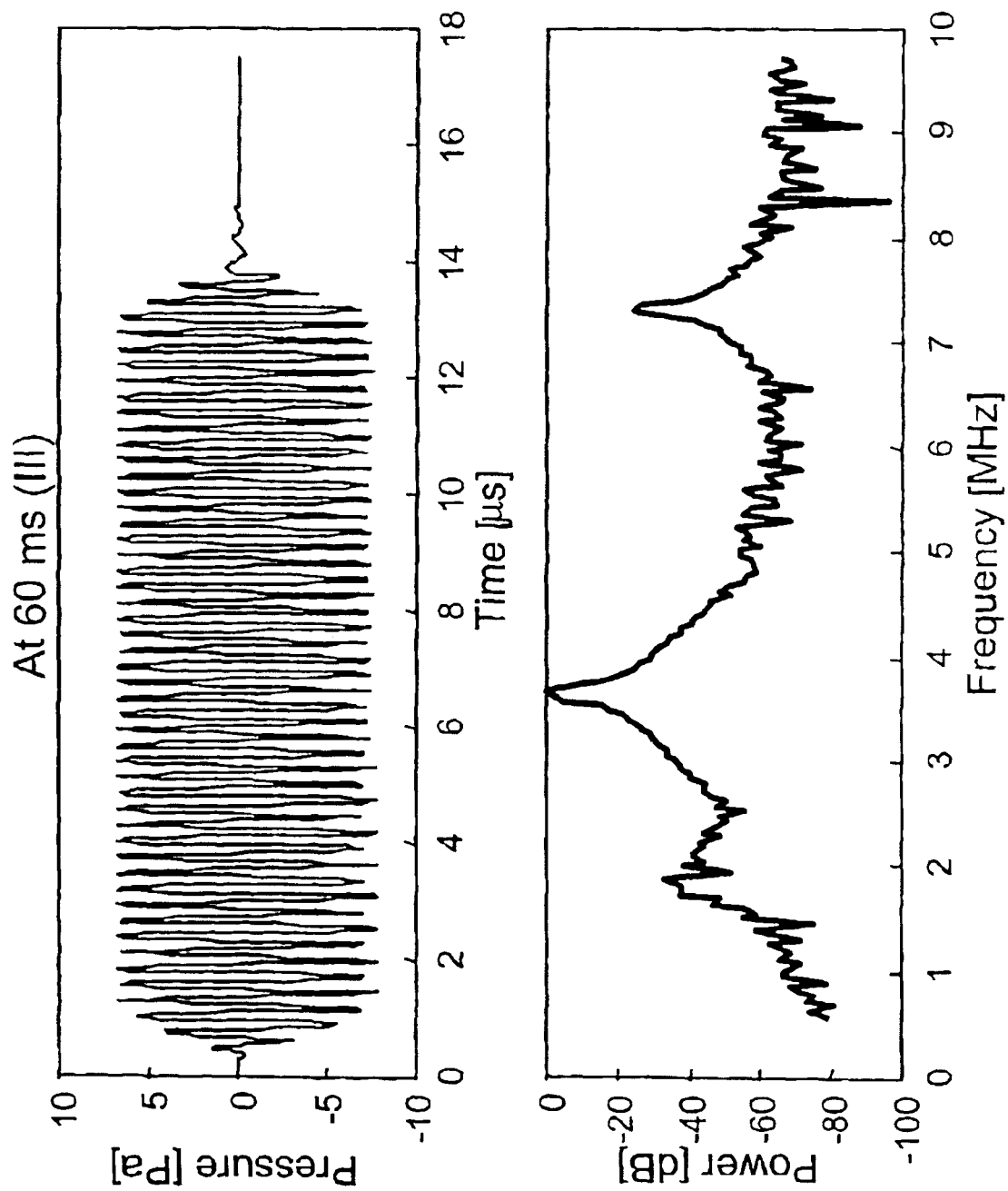
FIG. 3D. Sub- and ultraharmonic response and associated spectrum of a 2.2-$\mu$m air bubble, 60 ms after release.

In a gas-saturated liquid, the dissolution of micron-sized free-gas bubbles is caused by a difference in gas concentration between the gas inside the bubble and inside the liquid due to surface tension and overpressure. In FIG. 2, for example, the radius-time curve for a 2.2-μm air bubble in water is simulated at values of the overpressure of 0 mmHg and 200 mmHg. It is assumed that temperature and gas concentration are constant. The disappearance time is 120.9 and 94.1 ms, respectively.

The ultrasound parameters for releasing free gas bubbles are tuned in such a way (e.g. by adjusting its frequency and/or amplitude) that the size of the released bubbles is larger than the subharmonic size. The subharmonic size of a gas bubble is defined as the radius of the bubble for which the resonance frequency equals half the transmitted frequency ($f_0$). After the release of known-size free-gas bubbles, gas dissolving into the surrounding liquid, i.e. the bubble size as a function of time, is monitored by means of ultrasound waves.

When the bubble size equals the subharmonic size, the response of the gas bubble to the monitoring ultrasound waves will show the appearance of subharmonics ($1/2f_0$, $1/3f_0$, $3/4f_0$ . . . ) of the transmitted frequency. Additionally, the response of the gas bubble to the ultrasound waves will show the appearance of ultraharmonics ($3/2f_0$, $5/2f_0$ . . . ) of the transmitted frequency.

This is advantageously illustrated in FIG. 3, which shows the response of a 2.2-μm air bubble to an ultrasound wave at different time instants during gas dissolution in the surrounding liquid at 0 mmhg overpressure (101.3 kPa). In this particular example, the subharmonic component is chosen to be $1/2f_0$ and the ultraharmonic component is chosen to be $3/2f_0$. FIG. 3A shows the radius-time curve of a 2.2-μm air bubble in water. The three dots, I, II and III correspond to a bubble size greater than subharmonic size, at subharmonic size and smaller than subharmonic size, respectively. The corresponding time and frequency responses are shown in FIGS. 3B, 3C and 3D for I, II and III, respectively.

Surprisingly, the sub- and ultraharmonic responses of gas bubbles are very sensitive to their sizes. Consequently, the sub- and ultraharmonic responses of gas bubbles are very sensitive to parameters that influence the bubble size. Measuring the change in bubble size due to gas dissolving in the surrounding liquid, by means of the response of sub- and/or ultraharmonics as a function of time, an improved estimation of the local pressure or other parameters can be made. It should be mentioned that the improved sensitivity for noninvasive measurement in a fluid-filled cavity, as shown in this invention, is only obtainable by the combination of the sub- and/or ultraharmonic response and the disappearance time of the released gas bubbles.

After the release of a free-gas bubble with a radius larger than the subharmonic size, the sub- and ultraharmonic response amplitude of the gas bubble will increase until it reaches a maximum and subsequently decrease until it disappears. The mean sub- or ultraharmonic response time is defined as the mean time (weighted by for example the energy or correlation coefficient of the sub- or ultraharmonic response) for sub- or ultraharmonics to appear after the release of the gas from the stabilized or encapsulated gas bubble. In formula form this is:

$$\overline{T} = \frac{\sum_{t=t_1}^{t_2} t \times E(t)}{\sum_{t=t_1}^{t_2} E(t)}, \quad (2)$$

where
$\overline{T}$=mean response time
t=time
E(t)=sub- or ultraharmonic energy or correlation at time t
$t_1, t_2$=time after the release of free-gas bubbles where the sub- or ultraharmonic energy is half the maximum energy.

As it is known by a person skilled in the art, absolute values of the local physical parameters can be derived from the mean response time, as calculated in equation 2, by comparing the calculated mean response time with predetermined values listed in calibration or look-up tables.

The sub- and/or ultraharmonic component of the transmit frequency can be obtained by standard signal processing techniques, like digital band-pass filtering of the time responses. The energy of the sub- and/or ultraharmonic components of the transmit frequency as a function of time is obtained by taking the sum of the squared value of the filtered responses at each time point. The correlation of the sub- and/or ultraharmonic components of the transmit frequency as a function of time is obtained by taking the correlation between the filtered responses at two successive time instants, at each time point.

Special care is taken to tune the monitoring ultrasound waves in such a way (e.g. by adjusting its frequency and/or amplitude) as to generate sub- and ultraharmonics and to minimize rupture or destruction of the encapsulated gas-filled microparticles.

The suspensions of encapsulated or stabilised gas bubbles useful in the present invention may be divided into three categories: stabilized microbubbles; microballoons (also called microcapsules); and microparticles. Free-gas bubbles are not included in these categories since, due to their rapid dissolution in the surrounding liquid; they are not stable enough to reliably deliver gas bubbles to the area of interest. Interest has accordingly been shown in methods of stabilising gas bubbles commonly used for echography and other ultrasonic studies, for example using emulsifiers, oils, thickeners or sugars, or by entrapping or encapsulating the gas or a precursor thereof in a variety of systems.

For the present invention, the encapsulated or stabilized gas bubbles are microbubbles bounded by a very thin envelope involving the surfactant bound at the gas to liquid interface, microballoons (microcapsules or gas-filled liposomes) bounded by a material envelope made of organic polymers or biodegradable water insoluble and at room temperature solid lipids or microparticles having gas contained therein or otherwise associated therewith (for example being adsorbed on the surface thereof and/or contained within voids, cavities or pores therein).

The first category, belonging to the class of microbubbles, specifically designates gas bubbles in suspension in a liquid preferably also containing surfactants or tensides to control the surface properties and the stability of the bubbles.

Preferably the microbubble suspension comprises a surfactant or a tenside, such as, for example, a polyoxyethylene-polyoxypropylene block copolymer surfactant such as Pluronic® or a polymer surfactant like that disclosed in U.S. Pat. No. 5,919,434. More preferably amphipathic compounds capable of forming stable films in the presence of water (or an aqueous carrier) and gas are used as surfactants in the stabilized microbubbles useful in the invention. Such compounds may include, for example a film forming lipid. The lipids, synthetic or naturally-occurring generally amphipathic and biocompatible, usable for preparing the gas-containing agents used in the present invention include, for example, fatty acids; lysolipids; phospholipids such as: phosphatidylcholine (PC) with both saturated and unsaturated lipids; including phosphatidylcholine such as dioleylphosphatidylcholine; dimyristoylphosphatidylcholine (DMPC), dipentadecanoylphosphatidylcholine, dilauroylphosphatidylcholine (DLPC); dipalmitoylphosphatidylcholine (DPPC); disteraoylphosphatidylcholine (DSPC); and diarachidonylphospha-tidylcholine (DAPC); phosphatidylethanolamines (PE), such as dioleylphosphatidylethanolamine, dipalmitoylphosphatidylethanolamine (DPPE) and distearoyl-phosphatidylethanolamine (DSPE); phosphatidylserine (PS) such as dipalmitoyl phosphatidylserine (DPPS), disteraoylphosphatidylserine (DSPS); phosphatidylglycerols (PG), such as dipalmitoylphosphatidylglycerol (DPPG), distearoylphosphatidylglycerol (DSPG); phosphatidylinositol; sphingolipids such as sphingomyelin; glycolipids such as gangliosides GM1 and GM2; glucolipids; sulfatides; glycosphingolipids; phosphatidic acids as dipaimitoylphosphatidic acid (DPPA) and distearoylphosphatidic acid (DSPA); fatty acids such as: palmitic acid; stearic acid; arachidonic acid; oleic acid; lipids bearing polymers, such as chitin, hyaluronic acid, polyvinylpirrolidone or polyethylene glycol (PEG), also referred as "pegylated lipids", with preferred lipids bearing polymers including DPPE-PEG (DPPE-PEG), which refers to the lipid DPPE having a PEG polymer attached thereto, including, for example, DPPE-PEG2000, which refers to DPPE having attached thereto a PEG polymer having a mean average molecular weight of about 2000; lipids bearing sulfonated mono- di-, oligo- or polysaccharides; cholesterol, cholesterol sulfate and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylamine; cardiolipin; phosholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes such as polyoxyethylene fatty acid esters, polyoxyethylene fatty alcohols, polyoxyethylene fatty alcohol ethers, polyoxyethylated sorbitan fatty acid esters, glycerol polyethylene glycol ricinoleate, ethoxylated soybean sterols, ethoxylated castor oil, polyoxyethylene-polyoxypropilene polymers, and polyoxyethylene fatty acid stearates; sterol aliphatic acid esters including cholesterol sulfate, cholesterol butyrate, cholesterol iso-butyrate, cholesterol palmitate, cholesterol stearate, lanosterol acetate, ergosterol palinitate, and phytosterol n-butyrate; sterol esters of sugar acids including cholesterol glucoronides, lanosterol glucoronides, 7-dehydrocholesterol glucoronide, ergosterol glucoronide, cholesterol gluconate, lanosterol gluconate, and ergosterol gluconate; esters of sugar acids and alcohols including lauryl glucoronide, stearoyl glucoronide, myristoyl glucoronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol dipaimitate, glycerol and glycerol esters including glycerol tripalmitate, glycerol distearate, glycerol tristearate, glycerol dimyristate, glycerol trimyristate; long chain alcohols including n-decyl alcohol, lauryl alcohol, myristyl alcohol, cetyl alcohol, and n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galacto-pyranoside; 6-(5-cholesten-3β-yloxy)hexyl-6-amino-6-deoxyl-1-thio-β-D-mannopyranoside; 12-(((7'-diethylaminocoumarin-3-yl) carbonyl)-methylamino)octadecanoic acid; N-[12-(((7'-diethylaminocoumarin-3-yl)carbonyl)methylamino) octadecanoyl]-2-aminopalmitic acid; N-succinyldioleylphosphatidylethanolamine; 1,2-dioleyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine and palmitoylhomocysteine, and/or combinations thereof.

Preferably, the lipid is a film forming phospholipid and more preferably the film forming phospholipid material may be selected from saturated phospholipids or synthetic non-saturated phospholipids or a mixture thereof. Examples of suitable phospholipids are saturated synthetic lecithins, such as, dimyristoylphosphatidylcholine, dipalmitoylphosphatidylcholine, distearoylphosphatidylcholine or diarachidoylphosphatidylcholine or unsaturated synthetic lecithins, such as dioleylphosphatidyl choline or dilinoleylphosphatidylcholine or mixed chains phosphatidylcholines such as for instance monooleylmonopalmitoylphosphatidylcholine, with saturated phospholipids being preferred. Even more preferably, the saturated phospholipid may be selected from saturated phosphatidic acid, saturated phosphatidylcholine, saturated phosphatidyl-ethanolamine, saturated phosphatidylserine, saturated phosphatidylglycerol, saturated phosphatidyl-inositol, saturated cardiolipin and saturated sphingomyelin. Particularly preferred are the saturated phospholipids selected in the following group: dimyristoylphosphatidylethanolamine, dipalmitoylphosphatidylethanolamine, distearoylphosphatidylethanolamine or diarachidoylphosphatidylethanolamine; or dioleylphosphatidylethanolamine or dilinoleylphosphatidylethanolamine, fluorinated analogues of any of the foregoing, mixtures of any of the foregoing, with saturated phosphatidylcholine being preferred.

Additives like cholesterol and other substances can optionally be added to one or more of the foregoing lipids in proportions ranging from zero to 50% by weight. Such additives may include other non-phospholipid surfactants that can be used in admixture with the film forming surfactants and most of which are known. For instance compounds like polyoxypropylene glycol and polyoxyethylene glycol as well as copolymers thereof, ergosterol, phytosterol, sitosterol, lanosterol, tocopherol, propyl gallate, ascorbyl palmitate and butylated hydroxytoluene, fatty acids such as myristic acid, palmitic acid, stearic acid, arachidic acid or their derivatives. Particularly preferred is palmitic acid. The amount of these non-film-forming surfactants is usually up to 50% by weight of the total amount of surfactants but preferably between 0 and 30%.

This category includes aqueous suspensions in which the gas bubbles are bounded at the gas/liquid interface by a very thin layer of surfactant bound at the gas to liquid interface. Easy-to-produce aqueous microbubble suspensions usable in the present invention are disclosed in, for example, EP 474833 (U.S. Pat. No. 5,271,928), U.S. Pat. Nos. 5,380,519, 5,531,980, 5,567,414, 5,643,553, 5,658,551, 5,911,972, incorporated herein by reference in their entirety. The suspensions contain film forming surfactants in laminar and/or lamellar form and, optionally, hydrophilic stabilisers. These microbubbles are stabilised by one or more mono-molecular layer(s) of amphipathic compounds i.e. compounds with hydrophilic and hydrophobic moieties. These patents also disclose a dry composition, which, upon admixing with an aqueous carrier liquid, will generate a sterile suspension of microbubbles thereafter usable in the present invention. Preferred suspensions contain phospholipids as film forming surfactants and, optionally, hydrophilic stabilizers. The total concentration of phospholipids may range from 0.01% to 20% and preferably comprised between 0.01–10% (w/w) of the total lipid concentration and even most preferably between 0.1–1% (w/w). The concentration of microbubbles may range from $10^7$ to $10^{10}$ bubbles/mL, with a preferred concentration of is between $10^8$ and $10^9$ bubbles/mL. The microbubble suspensions remain stable for months.

Preferred phospholipid monolayer stabilized microbubbles are also disclosed in for example, U.S. Pat. Nos. 5,445,813; 5,597,549; 5,686,060 (Schneider et al), U.S. Pat. Nos. 5,413,774; 5,578,292 (Schneider et al), U.S. Pat. Nos. 5,556,610; 5,846,518 (Yan et al) and U.S. Pat. No. 5,827,504 (Yan et al), incorporated herein by reference in their entirety.

Other microbubble suspensions useful in the invention include those disclosed in, for example, U.S. Pat. No. 5,798,091 (Trevino et al) and WO 97/29783 (Nycomed designating the US, also EP 881 915), incorporated herein by reference in their entirety.

For example, U.S. Pat. No. 5,798,091 discloses what is stated to be a gas emulsion comprising a plurality of bubbles surrounded by a layer of at least a first and a second surfactant. The first surfactant is a hydrophobic phospholipid or mixture of phospholipids having at least one acyl chain, which comprises at least 10 carbon atoms, which is at least about 5% w/w of the total surfactant. The second surfactant is may or may not also be a phospholipid or mixture of phospholipids, but which is more hydrophilic than the phospholipid or combination of phospholipid provided as the first surfactant. Preferred second surfactants may be selected from the group consisting of phospholipids, phosphocholines, lysophospholipids, nonionic surfactants, neutral or anionic surfactants, fluorinated surfactants, which can be neutral or anionic, and combinations of such emulsifying or foaming agents. Some specific examples of surfactants which are useful as the second surfactant include block copolymers of polyoxypropylene and polyoxyethylene (an example of such class of compounds is Pluronic, such as Pluronic F-68), sugar esters, fatty alcohols, aliphatic amine oxides, hyaluronic acid aliphatic esters, hyaluronic acid aliphatic ester salts, dodecyl poly(ethyleneoxy)ethanol, nonylphenoxy poly(ethyleneoxy) ethanol, derivatized starches, hydroxy ethyl starch fatty acid esters, salts of fatty acids, commercial food vegetable starches, dextran fatty acid esters, sorbitol fatty acid esters, gelatin, serum albumins, and combinations thereof. Also contemplated as a second surfactant are polyoxyethylene fatty acids esters, such as polyoxyethylene stearates, polyoxyethylene fatty alcohol ethers, polyoxyethylated sorbitan fatty acid esters, glycerol polyethylene glycol oxystearate, glycerol polyethylene glycol ricinoleate, ethoxylated soybean sterols, ethoxylated castor oils, and the hydrogenated derivatives thereof. In addition, nonionic alkylglucosides such as Tweens®, Spans® and Brijs® may also be used as the second surfactant.

In WO 9729783, there is provided a contrast agent for use in diagnostic studies comprising a suspension in an injectable aqueous carrier liquid of gas microbubbles stabilised by phospholipid-containing amphiphilic material characterised in that said amphiphilic material consists essentially of phospholipid predominantly comprising molecules with net charges. Desirably at least 75%, preferably substantially all of the phospholipid material in the contrast agents consists of molecules bearing a net overall charge under conditions of preparation and/or use, which charge may be positive or, more preferably, negative. Representative positively charged phospholipids include esters of phosphatidic acids such as dipalmitoylphosphatidic acid or distearoylphosphatidic acid with aminoalcohols such as hydroxyethylenediamine. Examples of negatively charged phospholipids include naturally occurring (e.g. soya bean or egg yolk derived), semisynthetic (e.g. partially or fully hydrogenated) and synthetic phosphatidylserines, phosphatidylglycerols, phosphatidylinositols, phosphatidic acids and cardiolipins. The fatty acyl groups of such phospholipids will typically each contain about 14–22 carbon atoms, for example as in palmitoyl and stearoyl groups. Lyso forms of such charged phospholipids are also useful, the term "lyso" denoting phospholipids containing only one fatty acyl group, this preferably being ester-linked to the 1 position carbon atom of the glyceryl moiety. Such lyso forms of charged phospholipids may advantageously be used in admixture with charged phospholipids containing two fatty acyl groups.

The preparation of a preferred gas-filled microbubble suspension useful in the invention can be done according to, for example, the methods described in the following patents: EP 554213; U.S. Pat. Nos. 5,413,774; 5,578,292; EP 744962; EP 682530; U.S. Pat. No. 5,556,610; EP 474833; U.S. Pat. Nos. 5,271,928; 5,380,519; 5,531,980; 5,567,414; EP 619743; U.S. Pat. Nos. 5,445,813; 5,597,549, incorporated by reference herein in their entirety.

Regardless of how the microbubble suspension is prepared, in order to permit free passage through the pulmonary system and to achieve resonance, it may be convenient to employ microbubbles having an average size of 0.1–10 µm. Microbubbles used in the present invention may be produced with a very narrow size distribution for the microbubble dispersion within the range preferred for echography, thereby greatly enhancing their effective echogenicity as well as their safety in vivo, and rendering the microbubbles of particular advantage in such application.

The second category includes contrast agents with a solid material envelope formed of natural or synthetic polymers. In this case, the gas filled bodies are referred to as microballoons. The term "microballoon" or "microcapsule" designates gas-filled bodies with a material boundary or envelope, i.e. a polymer membrane wall. Gas-filled liposomes according to, for example, U.S. Pat. No. 5,580,575 (Unger) also belong to this category and are incorporated herein by reference. More on these different formulations may be found in EP-A-0 324 938 (U.S. Pat. No. 4,844,882, Widder et al.), U.S. Pat. No. 5,711,933 (Bichon et al.), U.S. Pat. No. 4,900,540 (Ryan), U.S. Pat. No. 5,230,882 (Unger), U.S. Pat. No. 4,718,433 (Feinstein), U.S. Pat. No. 4,774,958 (Feinstein), WO 9501187 (MBI designating the US), U.S. Pat. No. 5,529,766 (Nycomed), U.S. Pat. No. 5,536,490 (Nycomed), U.S. Pat. No. 5,990,263 (Nycomed) the contents of which are incorporated herein by reference.

Microballoons, which may be particularly useful in the present invention, include pressure resistant microballoons bounded by a soft and elastic membrane, which can temporarily deform under variations of pressure and are endowed with enhanced echogenicity and are biodegradable.

For polymeric microballoon, the polymer, which constitutes the envelope or bounding membrane of the injectable microballoons can be selected from most hydrophilic, biodegradable physiologically compatible polymers. Such polymers include polysaccharides of low water solubility, polylactides and polyglycolides and their copolymers, copolymers of lactides and lactones such as e-caprolactone, γ-valerolactone and polypeptides. Other suitable polymers include poly-(ortho)esters (see for instance U.S. Pat. Nos. 4,093,709; 4,131,648; 4,138,344; 4,180,646 also incorporated herein by reference); polylactic and polyglycolic acid and their copolymers, for instance DEXON (see J. Heller, Biomaterials 1 (1980), 51, incorporated herein by reference in its entirety); poly(DL-lactide-co-γ-caprolactone), poly (DL-lactide-co-γ-valerolactone), poly(DL-lactide-co-g-butyrolactone), polyalkylcyanoacrylates; polyamides, polyhydroxybutyrate; polydioxanone; poly-β-aminoketones (Polymer 23 (1982), 1693, incorporated herein by reference in its entirety), polyphosphazenes (Science 193 (1976), 1214, incorporated herein by reference in its entirety); and polyanhydrides. References on biodegradable polymers can be found in R. Langer et al., Macromol. Chem. Phys. C23 (1983), 61–126, incorporated herein by reference in its entirety. Polyamino-acids such as polyglutamic and polyaspartic acids can also be used as well as their derivatives, i.e. partial esters with lower alcohols or glycols. One useful example of such polymers is poly-(t.butyl-glutamate). Copolymers with other amino-acids such as methionine, leucine, valine, proline, glycine, alamine, etc. are also possible. Recently some novel derivatives of polyglutamic and polyaspartic acid with controlled biodegradability have been reported (see U.S. Pat. Nos. 4,892,733; 4,888,398 and 4,675,381 incorporated herein by reference in their entirety). Biodegradable water insoluble and at room temperature solid lipids selected from a mono-, di- or tri-glycerides, fatty acids, sterols, waxes and the mixtures thereof may also be used for the manufacture of microballoons according to the invention (see WO 96/15815 incorporated herein by reference in its entirety). Non-biodegradable polymers for making microballoons can be selected from most water-insoluble, physiologically acceptable, bioresistant polymers including polyolefins (polystyrene), acrylic resins (polyacrylates, polyacrylonitrile), polyesters (polycarbonate), polyurethanes, polyurea and their copolymers. ABS (acryl-butadiene-styrene) is a preferred copolymer.

Properties of the membrane, for instance strength, elasticity and biodegradability, can be controlled. Additives can be incorporated into the polymer wall of the microballoons to modify the physical properties such as dispersibility, elasticity and water permeability. Among the useful additives, one may cite compounds which can "hydrophobize" the microballoons membrane in order to decrease water permeability, such as fats, waxes and high molecular-weight hydrocarbons. Additives, which improve dispersibility of the microballoons in the injectable liquid carrier, are amphipatic compounds like the phospholipids; they also increase water permeability and rate of biodegradability. The quantity of additives to be incorporated in the polymer forming the membrane of the present microballoons is extremely variable and depends on the needs. In some cases no additive is used at all, in other cases amounts of additives, which may reach about 20% by weight of the polymer, are possible.

The third category of stabilized or encapsulated gas bubbles are microparticles, suspensions of porous particles of polymers or other solids, which carry gas microbubbles, entrapped within the pores of the microparticles. These systems, which include aggregates of microparticles, have gas contained therein or otherwise associated therewith (for example being adsorbed on the surface thereof and/or contained within voids, cavities or pores therein, e.g. as described in EP 0122 624, EP 0123 235, EP 0365 467, U.S. Pat. Nos. 5,558,857, 5,607,661, 5,637,289, 5,558,85, 5,137, 928, WO 9521631 or WO 93/3809, incorporated by reference herein in their entirety.

The encapsulated or stabilised gas bubbles (stabilized microbubble, microballoon or microparticle suspensions) used in the present invention may conveniently be administered in a pharmaceutically acceptable aqueous liquid carrier. Suitable liquid carriers are water, aqueous solutions such as saline (which may advantageously be balanced so that the final product for injection is not hypotonic), or solutions of one or more tonicity adjusting substances such as salts or sugars, sugar alcohols, glycols and other non-ionic polyol materials (e.g. glucose, sucrose, sorbitol, mannitol, glycerol, polyethylene glycols, propylene glycols and the like). In practice all injectable compositions should also be as far as possible isotonic with blood. Hence, before injection, small amounts of isotonic agents may also be added to the suspensions of the invention. The isotonic agents are physiological solutions commonly used in medicine and they comprise aqueous saline solution (0.9% NaCl), 2,6% glycerol solution, 5% dextrose solution, etc.

Other excipients may if desired be present in the composition being dried or may be added on formulation for administration. Such excipients may for example include pH regulators, osmolality adjusters, viscosity enhancers, emulsifiers, bulking agents, etc. and may be used in conventional amounts.

The encapsulated or stabilised gas bubbles are filled with a gas or a gas mixture comprising a physiologically acceptable gas selected from the group consisting of fluorinated gases, including sulfur hexafluoride, trifluoromethylsulfur pentafluoride, Freons® (e.g. organic compounds containing one or more carbon atoms and fluorine such as $CF_4$, $CBrF_3$, $C_4F_8$, $CClF_3$, $CCl_2F_2$, $C_2F_6$, $C_2ClF_5$, $CBrClF_2$, $CBr_2F_2$, $C_3F_8$ and $C_4F_{10}$ and mixtures thereof), and perfluorocarbons; air; nitrogen; oxygen; carbon dioxide; hydrogen; nitrous oxide; inert gases such as helium, krypton, xenon, and argon; hyperpolarized gases; a low molecular weight hydrocarbon (e.g. containing up to 7 carbon atoms), for example an alkane such as methane, ethane, a propane, a butane or a pentane, a cycloalkane such as cyclobutane or cyclopentane, an alkene such as propene or a butene, or an alkyne such as acetylene; an ether; a ketone; an ester; a halogenated low molecular weight hydrocarbon (e.g. containing up to 7 carbon atoms); or a mixture of any of the foregoing. At least some of the halogen atoms in halogenated gases advantageously are fluorine atoms.

Biocompatible halogenated hydrocarbon gases may, for example, be selected from bromochlorodifluoromethane, chlorodifluoromethane, dichlorodifluoromethane, bromotrifluoromethane, chlorotrifluoromethane, chloropentafluoroethane, dichlorotetrafluoroethane and perfluorocarbons, e.g. perfluoroalkanes such as perfluoromethane, perfluoroethane, perfluoropropanes, perfluorobutanes (e.g. perfluoro-n-butane, optionally in admixture with other isomers such as perfluoro-isobutane), perfluoropentanes, perfluorohexanes and perfluoroheptanes, pefluorooctanes, perfluorononanes, perfluorodecanes; perfluoroalkenes such as perfluoropropene, perfluorobutenes (e.g. perfluorobut-2ene) and perfluorobutadiene; perfluoroalkynes such as perfluorobut-2-yne; and perfluorocycloalkanes such as perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane. Other halogenated gases include fluorinated, e.g. perfluorinated, ketones such as perfluoroacetone and fluorinated, e.g. perfluorinated, ethers such as perfluorodiethyl ether. Contrast agents containing sulphur hexafluoride, perfluorocarbons, such as for example, perfluoropropane or perfluorobutane or mixtures thereof with air, oxygen, nitrogen, helium or $CO_2$ are preferred, with $SF_6$ and $C_4F_{10}$ are particularly preferred.

The gas can be a mixture of the gases above defined. In particular the following combinations are particularly preferred: a mixture of gases (A) and (B) in which, at least one of the gases (B), present in an amount of between 0.5–41% by vol., has a molecular weight greater than 80 daltons and (B) is selected from the group consisting of $SF_6$, $CF_4$, $C_2F_6$, $C_2F_8$, $C_3F_6$, $C_3F_8$, $C_4F_6$, $C_4F_8$, $C_4F_{10}$, $C_5F_{10}$, $C_5F_{12}$ and mixtures thereof and (A) is selected from the group consisting of air, oxygen, nitrogen, carbon dioxide and mixtures thereof the balance of the mixture being gas A.

In addition, as discussed, the contrast agent may include a gas precursor (e.g. a compound or compound mixture which is partially in gaseous form (including vapour) at normal human body temperatures (37° C.) i.e. $C_5F_{12}$, $C_6F_{14}$, cyclohexane, cyclooctane, hexane, cyclopentane, etc.). Particularly preferred are gas precursors with boiling points between 20 and 80° C. The gas precursor may be used alone or in combination with a gas or another gas precursor.

The foregoing description will be more fully understood with reference to the following Examples. Such Examples, are, however, exemplary of methods of practising the present invention and are not intended to limit the scope of the invention.

EXAMPLES

Example 1

Figure 4:
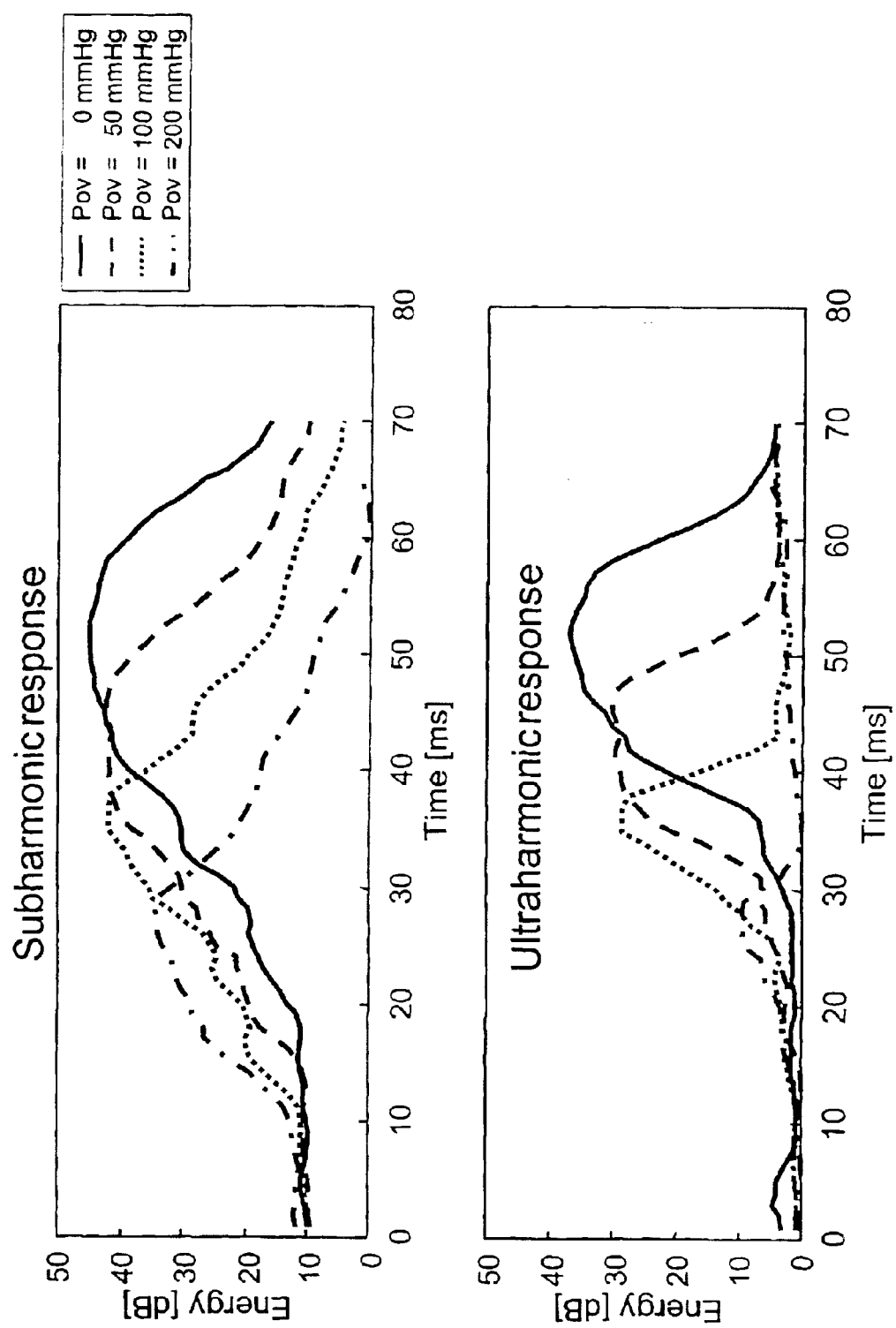
FIG. 4. Energy-time curves for different overpressures.

FIG. 4 shows the sub- and ultraharmonic energy curves (top and bottom, respectively) as a function of time for an air bubble with a radius of 2.2 µm as obtained by computer simulation. The curves were calculated, as described in the specification, for different values of the surrounding liquid pressure. The liquid pressure is indicated by the overpressure, i.e. the pressure value over the atmospheric pressure of 760 mmHg. The values for the overpressure were 0, 50, 100 and 200 mmHg. The different lines show the respective energy curves. From these curves the mean response time was calculated according to equation (2) and the values for the mean sub- and ultraharmonic response time are given in table 1 in the third and fourth column, respectively. As a reference, the time for the air bubble to completely disappear as a function of the overpressure is calculated by equation (1), and is given in the second column. By looking at the difference in sub- and ultraharmonic response time (column 3 and 4) for different pressures (difference between the rows), it is clear that with the new method similar or higher sensitivity can be obtained than by measuring the disappearance time. Additionally, a significant advantage of the new method is that the acquisition time will be much shorter (2–3 times) compared to the acquisition time for measuring the total disappearance time (column 2), which is important for real time application of the method.

TABLE 1

Disappearance time, td, mean response times for subharmonic, t_sub, and ultraharmonic, t_ul, as a function of the overpressure.

| Pov [mmHg] | td [ms] | t_sub [ms] | t_ul [ms] |
|---|---|---|---|
| 0 | 120.8 | 51.0 | 51.5 |
| 50 | 112.7 | 42.6 | 43.1 |
| 100 | 105.7 | 35.7 | 36.4 |
| 200 | 94.1 | 26.7 | 27.0 |

Example 2

This example shows the sensitivity of the new method to measure clinical relevant pressure differences of 10 mmHg, for an air bubble with a radius of 2.2 µm as obtained by computer simulation. The results of this example are shown in table 2. The overpressures range from 80 to 120 mmHg in steps of 10 mmHg. The difference in disappearance time (column 2 in table 2) ranges from 1.2 to 1.4 ms per 10 mmHg of pressure change. The difference in mean response time for the subharmonic (column 3 in table 2) ranges from 1.7 to 2.7 ms. The difference in mean response time for the ultraharmonic (column 4 in table 2) ranges from 2.1 to 2.8 ms. This means that by using the new method, the sensitivity increased by 40–100%, compared to methods that consider the complete disappearance of gas bubbles.

TABLE 2

Disappearance time, td, mean response times for subharmonic, t_sub, and ultraharmonic, t_ul, as a function of the overpressure.

| Pov [mmHg] | td [ms] | t_sub [ms] | t_ul [ms] |
|---|---|---|---|
| 80 | 108.4 | 40.2 | 41.3 |
| 90 | 107.0 | 37.5 | 38.5 |
| 100 | 105.7 | 35.7 | 36.4 |
| 110 | 104.4 | 34.0 | 34.0 |
| 120 | 103.2 | 32.1 | 31.5 |

We claim:

1. A noninvasive measuring method for remotely determining local physical parameters of a fluid-filled cavity, based on the combined use of encapsulated or stabilized gas bubbles and ultrasound waves, comprising the steps of:
    a) administering encapsulated or stabilized gas bubbles to a fluid filled cavity;
    b) applying a first ultrasound pulsed wave or a train of pulsed waves to the fluid tilled cavity to destroy the encapsulated or stabilized gas bubbles and generate free-gas bubbles;
    c) applying a second ultrasound pulsed wave or train of pulsed waves at a frequency chosen for exciting the sub- and/or ultraharmonic response of the free-gas bubbles;
    d) determining the mean sub- and/or ultraharmonic response time corresponding to the mean time for sub- or ultraharmonics to appear after the generation of the free gas bubbles from the encapsulated or stabilized bubbles; and
    e) determining a value for a local physical parameter on the basis of the response time of step d).

2. The measuring method according to claim 1, characterised in that the first ultrasound pulsed wave or train of pulsed waves is tuned in such a way that the size of the released free-gas bubbles is larger than the subharmonic size.

3. The measuring method according to claim 1 or 2, characterised in that the frequency and amplitude of the first ultrasound pulsed wave or train of pulsed waves can be chosen independently of the second ultrasound pulsed wave or train of pulsed waves.

4. The measuring method according to claim 1, characterised in that the frequency and amplitude of the second ultrasound pulsed wave or train of pulsed waves can be chosen and independently of the first ultrasound pulsed wave or train of pulsed waves.

5. The measuring method according to any one of the claims 1 or 2, wherein the local parameters are selected from the group consisting of the pressure, the temperature and the gas concentration.

6. The measuring method according to claim 1, wherein the encapsulated or stabilized gas bubbles are selected from the group consisting of microbubbles bounded by a very thin envelope involving the surfactant bound at the gas to liquid interface, microballoons bounded by a material envelope made of organic polymers or biodegradable water insoluble and at room temperature solid lipids and microparticles of polymers or other solids, which carry gas microbubbles, entrapped within or associated with the pores of the microparticles.

7. The measuring method according to claim 6, in which the encapsulated or stabilised gas bubbles comprise gas or a gas mixture selected from the group consisting of sulfur hexafluoride, a perfluorocarbon, air, nitrogen, carbon dioxide, helium, krypton, xenon, argon, methane, hyperpolarized helium, hyperpolarized xenon and mixtures thereof.

8. The measuring method according to claim 7, in which the encapsulated or stabilized gas bubbles comprise a perfluorocarbon selected from the group consisting of perfluoromethane, perfluoroethane, perfluoropropane, perfluorobutane, perfluorocyclobutane, perfluoropentane, perfluorohexane and mixtures thereof.

9. The measuring method according to claim 6, wherein at least one of the surfactants comprises a film-forming phospholipid.

10. The measuring method according to claim 9, wherein the phospholipid film forming surfactant is selected from the group consisting of a saturated phospholipid, a synthetic non-saturated phospholipid and mixtures thereof.

11. The measuring method according to claim 10, wherein the phospholipid film forming surfactant is a saturated phospholipid selected from the group consisting of saturated phosphatidic acid, saturated phosphatidylcholine, saturated phosphatidyl-ethanolamine, saturated phosphatidylserine, saturated phosphatidylglycerol, saturated phosphatidylinositol, cardiolipin and sphingomyelin.

12. The measuring method according to claim 6, which the encapsulated or stabilized gas bubble is a microballoon bounded by a polymer selected from the group consisting of polylactic or polyglycolic acid and their copolymers, denaturated serum albumin, denaturated haemoglobin, polycyanoacrylate, and esters of polyglutamic and polyaspartic acids or a biodegradable water insoluble and at room temperature solid lipid selected from a mono-, di- or triglycerides, fatty acids, sterols, waxes and the mixtures thereof.

13. The measuring method according to claim 12, in which the microballoon is bounded by a saturated triglycerides selected from the group consisting of tristearine, tripalmitine or mixtures thereof with other glycerides.

14. A method of diagnostic ultrasound for determining local physical parameters of a fluid-filled cavity "in situ" which comprises the steps of:
  a) administering to a subject a fluid agent containing encapsulated or stabilized gas bubbles;
  b) applying a first ultrasound pulsed wave or a train of pulsed waves to the fluid-filled cavity to destroy the encapsulated or stabilized gas bubbles and generate free-gas bubbles;
  c) applying a second ultrasound pulsed wave or train of pulsed waves around a frequency specifically chosen for exciting the sub- and/or ultraharmonic response of the free-gas bubbles;
  d) determining the mean sub- and/or ultraharmonic response time corresponding to the mean time for sub- or ultraharmonics to appear after the generation of the free gas bubbles from the encapsulated or stabilized bubbles; and
  e) determining a value for a local physical parameter on the basis of the response time of step d).

15. The method according to claim 14, wherein said subject is a vertebrate and said fluid agent containing encapsulated or stabilised gas bubbles is introduced into the vasculature or into a body cavity of said vertebrate.

* * * * *